US012800076B2

(12) United States Patent
Le Quere

(10) Patent No.: US 12,800,076 B2
(45) **Date of Patent: *Nov. 17, 2026**

(54) ASEPTIC COUPLING DEVICE FOR A TUBE

(71) Applicant: PARKER HANNIFIN EMEA SARL, Etoy (CH)

(72) Inventor: Philippe Le Quere, Betton (FR)

(73) Assignee: PARKER HANNIFIN EMEA SARL, Etoy (CH)

( * ) Notice: Subject to any disclaimer, the term of this patent is extended or adjusted under 35 U.S.C. 154(b) by 706 days.

This patent is subject to a terminal disclaimer.

(21) Appl. No.: 18/257,200

(22) PCT Filed: Dec. 16, 2021

(86) PCT No.: PCT/EP2021/086312
§ 371 (c)(1),
(2) Date: Jun. 13, 2023

(87) PCT Pub. No.: WO2022/129413
PCT Pub. Date: Jun. 23, 2022

(65) Prior Publication Data

US 2024/0044428 A1 Feb. 8, 2024

(30) Foreign Application Priority Data

Dec. 16, 2020 (FR) ....................................... 2013403

(51) Int. Cl.
*F16L 25/00* (2006.01)
*A61M 39/04* (2006.01)
(Continued)

(52) U.S. Cl.
CPC ......... *F16L 25/0018* (2013.01); *A61M 39/04* (2013.01); *A61M 39/18* (2013.01);
(Continued)

(58) Field of Classification Search
CPC ...... A61M 39/04; A61M 39/10; A61M 39/18; A61M 39/26; A61M 25/0014;
(Continued)

(56) References Cited

U.S. PATENT DOCUMENTS 4,030,494 A * 6/1977 Tenczar .................. F16L 37/02 285/21.2
5,697,652 A * 12/1997 Nishikawa ............ F16L 37/098 285/423

(Continued)

FOREIGN PATENT DOCUMENTS

FR 2953903 A1 6/2011
WO 98/50105 A1 11/1998

(Continued)

OTHER PUBLICATIONS

International Search Report and Written Opinion of the International Searching Authority for corresponding International Patent Application No. PCT/EP2021/086312, mailed Mar. 17, 2022.

*Primary Examiner* — Michael J Tsai
*Assistant Examiner* — Evelyn A Thoman
(74) *Attorney, Agent, or Firm* — Renner, Otto, Boisselle & Sklar, LLP

(57) ABSTRACT

An aseptic coupling device for a tube includes a tubular insert defining a fluid channel and having a first end segment configured for connection to the tube and a second end segment extending outwardly. A cantilevered rod extends axially within the channel and projects from the second end segment. An annular body is mounted on the insert and cooperates with the insert to define a housing that receives an annular sealing element. The sealing element is deformable between a first state, in which a flow section greater than a cross-section of the rod is defined, and a second state, in which the sealing element tightly surrounds the rod under axial compression to block fluid flow. The body is movable (Continued)

between a projecting position and a flush position to selectively compress the sealing element. A coupling assembly includes two such devices for aseptically connecting tubes.

7 Claims, 9 Drawing Sheets

(51) Int. Cl.
*A61M 39/18* (2006.01)
*F16L 29/00* (2006.01)
*F16L 37/092* (2006.01)
*A61M 39/10* (2006.01)

(52) U.S. Cl.
CPC .......... *F16L 29/007* (2013.01); *F16L 37/092* (2013.01); *A61M 39/10* (2013.01); *F16L 2201/44* (2013.01)

(58) Field of Classification Search
CPC .......... A61M 25/0097; A61M 25/0111; A61M 25/1025; A61M 39/14; A61M 39/16; A61M 39/162; A61M 39/165; A61M 2039/1072; A61M 2039/1077; A61M 2039/1094; F16L 37/098; F16L 37/0985; F16L 25/0018; F16L 2201/44; F16L 37/0841
See application file for complete search history.

(56) References Cited

U.S. PATENT DOCUMENTS

| | | | | | |
|---|---|---|---|---|---|
| 8,491,016 | B2 * | 7/2013 | Williams | F16L 37/00 285/377 |
| 2011/0240158 | A1 * | 10/2011 | Py | F16L 41/02 29/428 |
| 2012/0192968 | A1 * | 8/2012 | Bonnal | A61M 39/1011 137/454.2 |
| 2015/0260325 | A1 * | 9/2015 | Quick | F16L 37/26 285/326 |
| 2019/0081426 | A1 * | 3/2019 | Chavakula | H01R 13/6691 |

FOREIGN PATENT DOCUMENTS

| | | | |
|---|---|---|---|
| WO | 2012126858 | A1 | 9/2012 |
| WO | 2013/147688 | A1 | 10/2013 |
| WO | 2017/102482 | A1 | 6/2017 |

* cited by examiner

II–II

III–III

ASEPTIC COUPLING DEVICE FOR A TUBE

This application is a national phase of International Application No. PCT/EP2021/086312 filed Dec. 16, 2021, which claims priority to French Application No. 2013403 filed Dec. 16, 2020, each of which is hereby incorporated herein by reference in its entirety.

The present invention relates to the field of transporting liquid or gaseous fluids, and more particularly to an aseptic coupling device for coupling together two sterile tubes.

BACKGROUND OF THE INVENTION

Coupling assemblies are known for connecting together sterile pipes that are connected to circuit elements in the pharmaceutical industry, such as filters, centrifuges, pumps, tanks made of flexible plastics material, or processing containers such as bio-processors.

Such an assembly generally comprises two coupling devices for connecting together after each of them has been attached to a respective pipe end. Each device comprises a tubular body defining a channel arranged to receive the pipe end. The body has a front face with an annular sealing element securely fastened thereto and with which the pipe end is come into leaktight contact. The sealing element is covered in a protective film in the form of a strip that is folded in half with one portion removably adhering to a free side flank of the sealing element and with another portion forming a pull-tongue projecting from the first portion.

After the pipe ends have been engaged in the bodies, the devices are placed facing each other on the same axis, and they are then moved towards each other until the protective films come into contact and the sealing elements are lightly compressed. Removing the protective films simultaneously by pulling on the tongues causes the lateral flanks of the sealing elements to be put into contact with each other, and thus causes an aseptic channel to be formed for passing fluid between the two pipes. The devices are moved closer together prior to locking the relative positions of the devices by means of a clamp.

At the end of the processes of manufacturing a batch of pharmaceuticals, all of the pipes and the coupling devices are generally removed and incinerated. Reconditioning them (washing, sterilizing . . . ) is found to be expensive and runs the risk of damaging the devices (wear, breakage, or even loss of a component).

Nevertheless, it is found that such devices, which have numerous components, are found to be particularly expensive for single use only, particularly when that use is of short duration.

It would also be desirable to limit, or even to eliminate, any flow of fluid remaining trapped in the pipes while the devices are being disconnected. To do this, proposals have been made to fit the coupling devices with valves. Specifically, washable and reusable coupling devices are known that include valves provided for this purpose. Nevertheless it would not be economically viable to fit disposable coupling devices with such valves.

OBJECT OF THE INVENTION

An object of the invention is thus to provide an aseptic coupling device for a tube that enables the above-mentioned problems to be obviated, at least in part.

SUMMARY OF THE INVENTION

To this end, the invention provides an aseptic coupling device for a tube, the device comprising:

- a tubular insert defining a channel and having both a first end segment provided with means for connecting it to the tube and also a second end segment for extending outside the tube, the tubular insert being provided with a cantilevered rod extending axially inside the channel so as to have a free end portion projecting out from the second end segment of the insert; and an annular body comprising both a first end
- segment mounted on the second end segment of the insert and also a second end segment projecting axially from the second end segment of the insert so as to co-operate therewith to define a housing in register with the free end portion of the rod for receiving an annular sealing element that is placed between a front face of the second end segment of the insert and an internal lip of the second segment of the annular body.

According to the invention:

- the annular sealing element is deformable between a first state in which the sealing element defines a flow section greater than the cross section of the rod and a second state in which the sealing element tightly surrounds the rod, the sealing element being arranged to be taken from its first state to its second state under the effect of axial compression.
- the sealing element has a front face projecting from the second segment of the annular body with a protective film removably fastened thereto, the film having a pull-tongue folded down thereon with a first end connected to an edge of the protective film and a second end projecting from the edge of the film that is opposite from the first end of the pull-tongue; and
- the first end segment of the body is mounted on the insert so as to be movable axially between a projecting position in which it projects axially from the insert and in which the sealing element is in its first state, and a flush position in which it is flush with the insert and in which the sealing element is compressed axially sufficiently to be in its second state.

Thus, the sealing element serves both to seal the coupling of the tube and to shut the channel off completely, thereby limiting the number of components of the device while preventing the fluid that has remained trapped in the tube from flowing when the device is disconnected.

According to a particular characteristic of the invention, the device includes means for locking the body in the projecting position and in the flush position.

According to another particular characteristic of the invention, the device includes pre-coupling and coupling means for engaging another coupling device.

In particular manner, the pre-coupling and coupling means comprise at least one locking tab projecting axially from a front face of the body and including at least two serrations at a free end for co-operating with an edge of the other coupling device.

The invention also provides a coupling assembly for coupling together two tubes, the coupling assembly comprising two such coupling devices.

Advantageously, the two coupling devices are identical.

The invention also provides a method of coupling together two tubes by means of such a coupling assembly, the method comprising the following steps:

- placing the devices to face each other axially;
- moving the devices towards each other until the pull-tongues are in contact with each other and the protective films are pressed against the front faces of the bodies;

removing the protective films by pulling simultaneously on the pull-tongues; and moving the devices towards each other again until the bodies are pressed against each other.

BRIEF DESCRIPTION OF THE DRAWINGS

The invention can be better understood in the light of the following description, which is purely illustrative and non-limiting, and which should be read with reference to the accompanying drawings, in which.

DETAILED DESCRIPTION OF THE INVENTION

The invention is described below in application to coupling together a first sterile tube 100 forming a first fluid transport duct and a second fluid transport duct formed by a second sterile tube 200.

With reference to FIGS. 4A to 4D, in a first particular embodiment of the invention, a fluid coupling assembly given overall reference 1 comprises two coupling devices 10 for acting together to provide an aseptic connection between the first tube 100 and the second tube 200. The two devices 10 are identical, and in the figures they are distinguished by adding a letter A or B.

Figure 1:
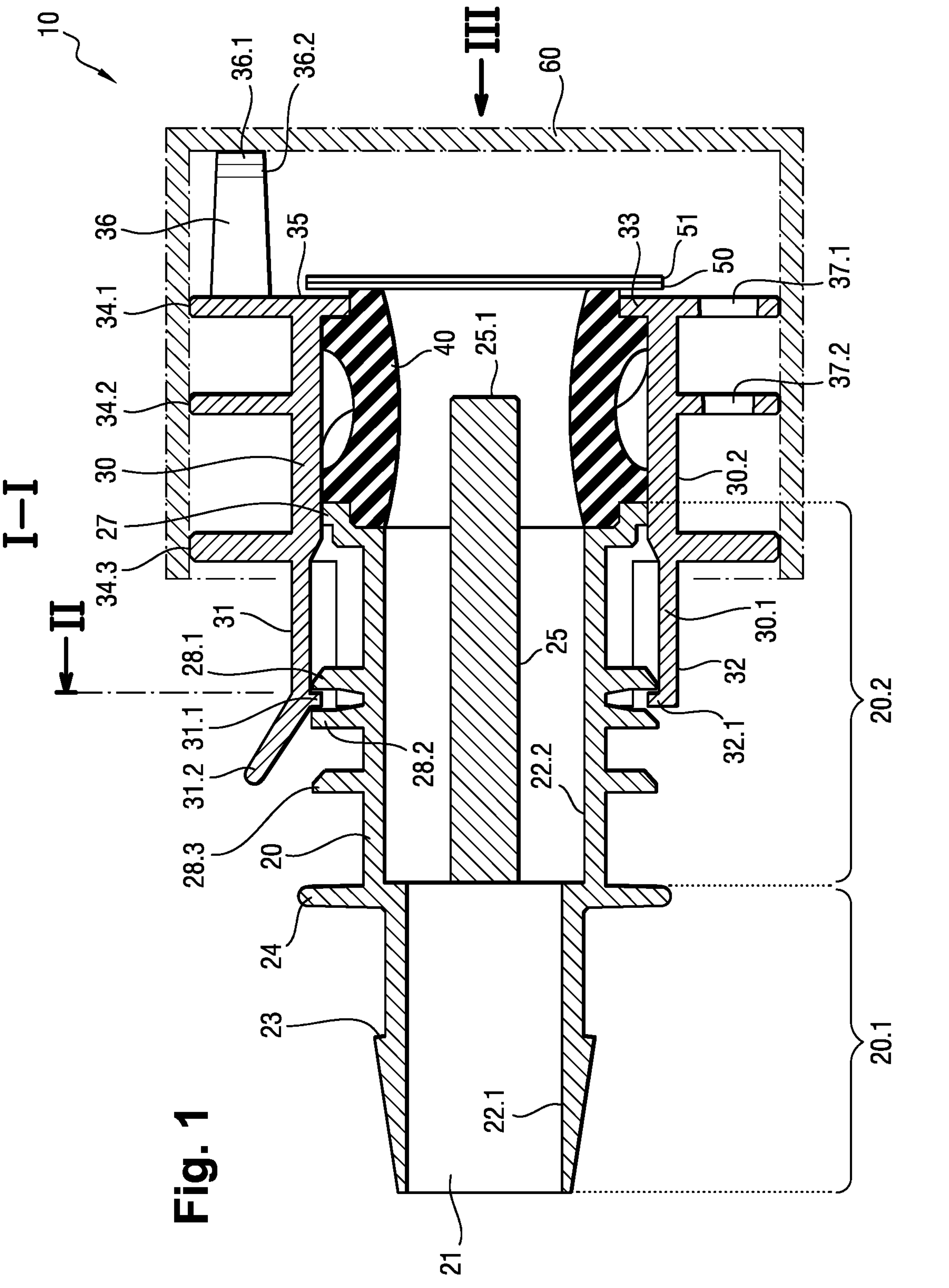
FIG. 1 is an axial section view of a coupling device in a particular embodiment of the invention.

As shown in FIG. 1, each device 10 comprises a tubular endpiece or insert 20 defining a fluid-passing channel 21.

The insert 20 has a first end segment 20.1 defining a first bore 22.1 forming a portion of the channel 21. The first segment 20.1 has a conically-shaped external projection 23 and a collar 24, respectively forming a spigot for anchoring it in the tube 100 or 200, and an abutment for stopping insertion into said tube 100 or 200.

Figure 2:
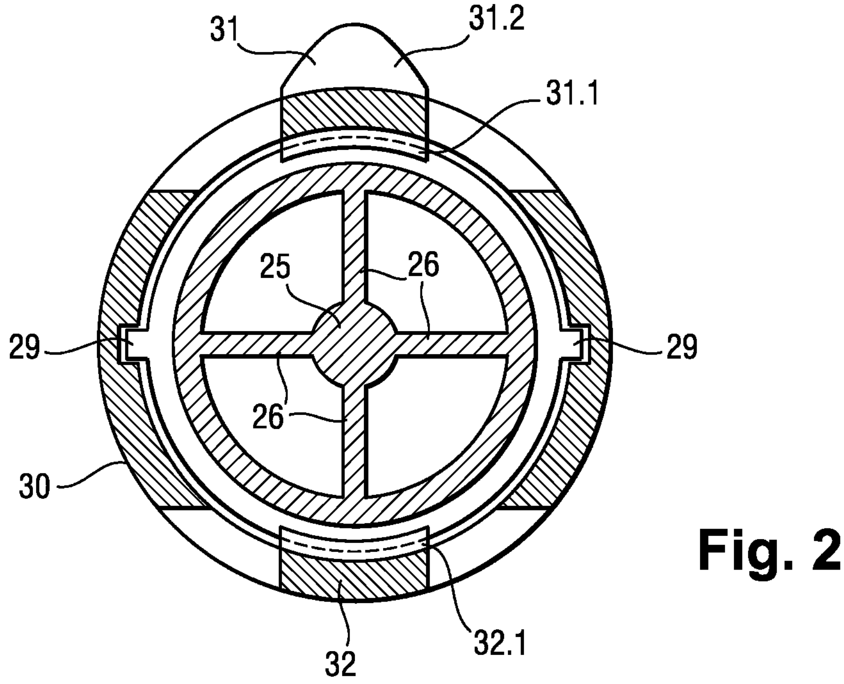
FIG. 2 is a cross-section view of the coupling device shown in FIG. 1.

The insert 20 has a second end segment 20.2 defining a second bore 22.2 having the same axis as the first bore 22.1 and forming a portion of the channel 21. The second segment 20.2 is provided internally with a cantilevered rod 25 of cylindrical shape extending axially inside the channel 21 so that a free end portion 25.1 of the rod projects out from the second segment 20.2 of the insert 20. As shown in FIG. 2, the rod 25 is connected to the second bore 22.2 via four vanes 26 uniformly distributed around said rod 25. In this example, the diameter of the rod 25 is such that the fluid flow section of the channel 21 is substantially identical in the first segment 20.1 and in the second segment 20.2.

The second segment 20.2 of the insert 20 is also provided externally both with a collar 27 arranged at a free end of said second segment 20.2, and also with three detent rings 28.1, 28.2, and 28.3 having substantially the same outside diameters about the axis. The collar 27 defines a front face of the second segment 20.2 of the insert 20, and it forms first centering means for centering a tubular body 30 mounted on the insert 20. The detent rings 28.1, 28.2, and 28.3 form both second centering means for centering the body 30 on the insert and also locking means for locking the body 30 in position on the insert 20 as described below.

The body 30 has both a first end segment 30.1 mounted on the second segment 20.2 of the insert 20, and also a second end segment 30.2 projecting axially from said second segment 20.2 of the insert 20.

The first segment 30.1 has four axial slots extending from a free edge of the first segment 30.1 so as to define between them two diametrically-opposite blades 31 and 32, each having one end secured to the remainder of the first segment 30.1 and an opposite end with an internal tooth 31.1 or 32.1 co-operating with a lateral flank of the first detent ring 28.1. The blades 31 and 32 are elastically deformable between a rest state in which the teeth 31.1 and 32.1 leave a through section smaller than the diameter of the detent rings 28.1, 28.2, and 28.3 of the insert 20, and a deformed state in which said teeth 31.1 and 32.1 leave a through section greater than the diameter of said detent rings 28.1, 28.2, and 28.3. The blade 31 differs from the blade 32 in that it includes an extension 31.2 at its free end that is arranged to receive a lifting force enabling the blade 31 to be put into its deformed state.

The detent rings 28.1, 28.2, and 28.3 of the insert have outer peripheries that are chamfered so as to avoid preventing the body 30 being mounted on the insert and so as to avoid preventing the body 30 moving axially from a projecting position in which the teeth 31.1 and 32.1 of the blades 31 and 32 are co-operating with the lateral flank of the first detent ring 28.1 (FIGS. 1 and 4A to 4D) to a flush position of the insert 20 in which said teeth 31.1 and 32.1 are co-operating with a lateral flank of the third detent ring 28.3 (FIGS. 5B and 5C), but also so as to prevent the body 30 from being moved axially from its flush position towards its projecting position. As can be seen in FIG. 1, the periphery of only the second detent ring 28.2 is locally not chamfered so as to prevent the body being moved axially from its projecting position to its flush position unless a lifting force is applied to the blade 31 that is sufficient to put it in its deformed state.

As shown in FIG. 2, the periphery of each of the detent rings 28.1, 28.2, and 28.3 has two diametrically-opposite projections 29 arranged to be received in two grooves formed in the body 30 so as to constrain the body 30 and the insert 20 together in rotation.

The second segment 30.2 of the body 30 co-operates with the second segment 20.2 of the insert 20 to define a housing in register with the end portion 25.1 of the rod for receiving an annular sealing element 40 that is placed between the front face of the second segment 20.2 formed by the collar 27 and an inwardly-projecting annular lip 33 of the second segment 30.2 arranged at a free end of said second segment 30.2.

The second segment 30.2 of the body 30 is provided externally with three fins 34.1, 34.2, and 34.3 forming means for gripping the device 10. The fins 34.1, 34.2, and 34.3 are coaxial about the axis and they have outside diameters that are substantially identical. The first grip fin 34.1 projects radially in register with the lip 33, and together they define a front face 35 of the body for co-operating with the front face of the body of another device 10.

It should be observed that when the body 30 is in the flush position, the front face 35 of said body 30 and the free end of the end portion 25.1 of the rod 25 lie substantially in the same plane in this example.

Figure 3:
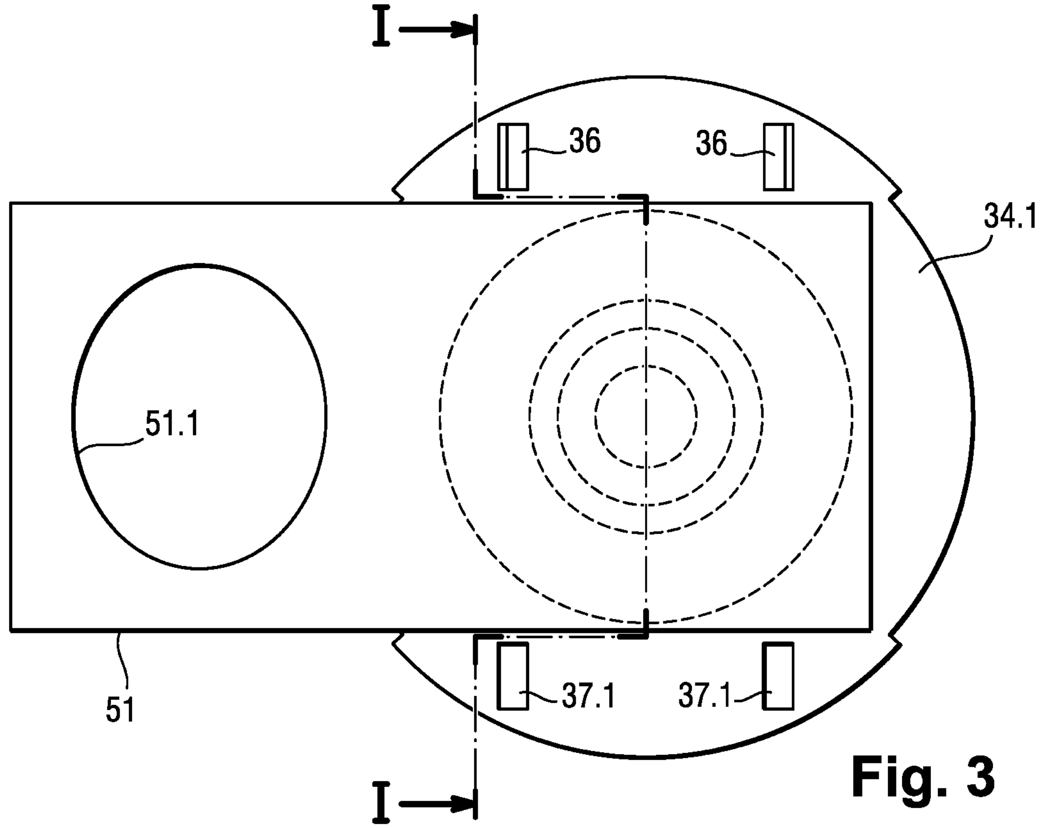
FIG. 3 is an end view of the coupling device shown in FIG. 1.

Two elastically-deformable locking tabs 36, which are substantially rectangular in the example, project axially from the front face 35 of the body 30, in the vicinity of its periphery. As shown in FIG. 3, the locking tabs 36 are symmetrical and extend parallel to the plane of FIG. 1. The locking tabs 36 have free ends, each having an outside surface with two serrations 36.1 and 36.2 for providing the device 10 and the other device 10 both with pre-coupling and with coupling.

The first and second fins 34.1 and 34.2 of the body are respectively provided with two first openings 37.1 and two second openings 37.2 of substantially rectangular shape, each for receiving a portion of a corresponding locking tab 36 of the other device 10. The openings 37.1 in the first fin 34.1 are arranged in the vicinity of the periphery of the collar 37, and they are diametrically opposite the locking tabs 36. The openings 37.2 in the second fin 34.2 are in register with the openings 37.1 in the first fin 34.1, and each has an edge for co-operating with the serrations 36.1 and 36.2 of the corresponding locking tab 36 of the other device 10.

The sealing element 40 is in leaktight contact with the front face of the second segment 20.2 and with an inside flank of the lip 33 facing said front face. The sealing element 40 is deformable from a first state in which it defines a flow section greater than the cross-section of the rod 25 of the insert 20, and a second state in which it tightly surrounds the rod 25, and it is arranged to be taken from its first state to its second state under the effect of axial compression. Such a sealing element is known from Document EP2569665.

When the body 30 is moved axially from its projecting position to its flush position, the insert 20 compresses the sealing element 40 hard enough against the lip 33 to take it from its first state to its second state.

The sealing element 40 has a front face that projects from the second segment 30.2 of the body 30 and that has a protective film 50 removably fastened thereto, the protective film 50 having a pull-tongue 51 folded down onto it to enable the protective film 50 to be removed without being touched. The pull tongue 51 has a first end connected to one edge of the protective film and a second end projecting from an edge of the protective film 50 opposite from the first end of the tongue 51. In its center, the second end of the tongue 51 has a hole 51.1 shaped to allow a finger to pass through said hole 51.1 in order to make the tongue 51 easier to grip.

In order to avoid any deterioration or contamination of the sealing element 40 during storage and transport of the device 10, a protective cover 60 is removably mounted on the second segment 30.2 of the body 30. By way of example, the cover 60 may be arranged to clip elastically on the third fin 34.3, and is to be taken off immediately before coupling the device 10 to the other device 10.

It should be observed that the entire device 10 is sterilized in the factory so as to be exempt from any contamination before being stored.

The operation of the coupling assembly 1 is described below with reference to FIGS. 4A to 5C.

The end segment 20.1 of the first device 10A is initially engaged in the first tube 100 until it comes into abutment against the collar 24 of said first device 10A. Likewise, the end segment 20.1 of the second device 10B is engaged in the second tube 200 until it comes into abutment against the collar 24 of said second device 10B, such that the first and second devices 10A and 10B are anchored respectively in the first and second tubes 100 and 200.

The protective covers 60 of the first and second devices 10A and 10B are then removed from the bodies 30, thereby revealing in particular the locking tabs 36 and the openings 37.1 and 37.1 of said bodies 30.

Figure 4A:
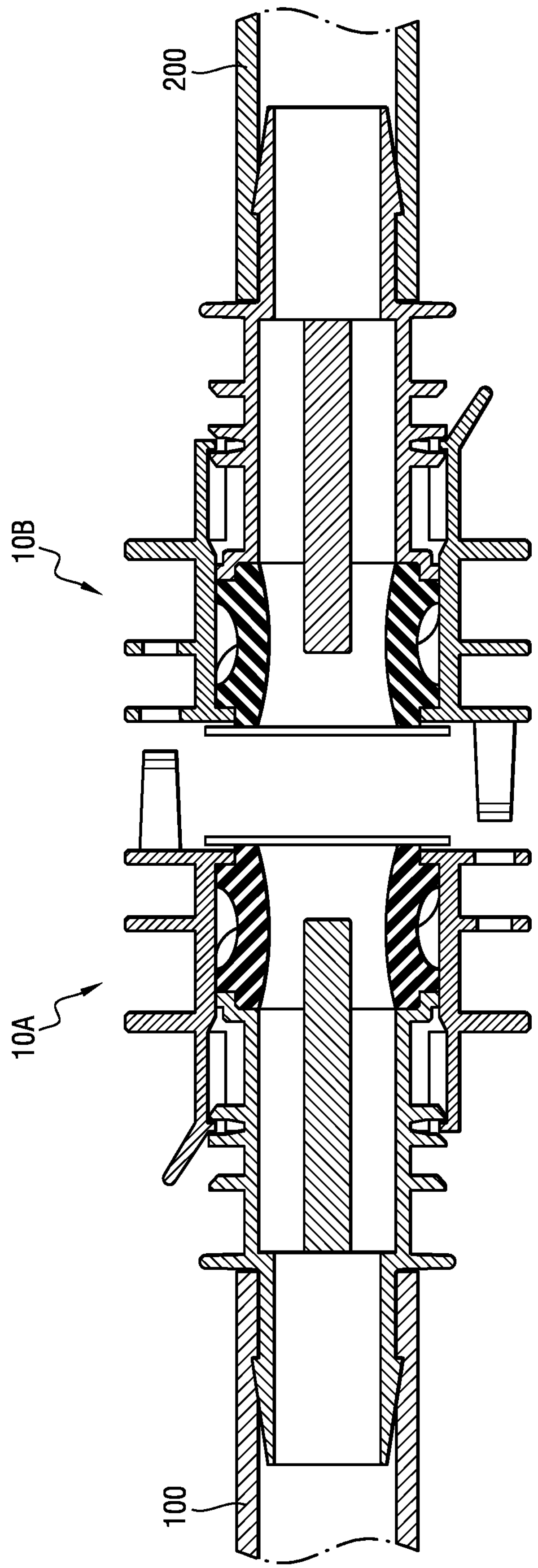
FIG. 4A is an axial section view of a coupling assembly in a particular embodiment of the invention, prior to connection.

Thereafter, the first and second devices 10A and 10B are presented facing each other along a common axis, with the first device 10A being turned through 180° about the axis relative to the second device 10B so that the locking tabs 36 and the openings 37.1 and 37.2 of the first device 10A are respectively facing the openings 37.1 and 37.2 and the locking tabs 36 of the second device 10B (FIG. 4A).

In a first stage, the first and second devices 10A and 10B are moved towards each other until the pull tongues 51 of the first and second devices 10A and 10B come into contact, with each of the openings 37.1 and 37.1 in the first device 10A then receiving a portion of a respective one of the locking tabs 36 of the second device 10B, and with each of the openings 37.1 and 37.2 in the second device 10B then receiving a portion of a respective one of the locking tabs 36 of the first device 10A.

Figure 4B:
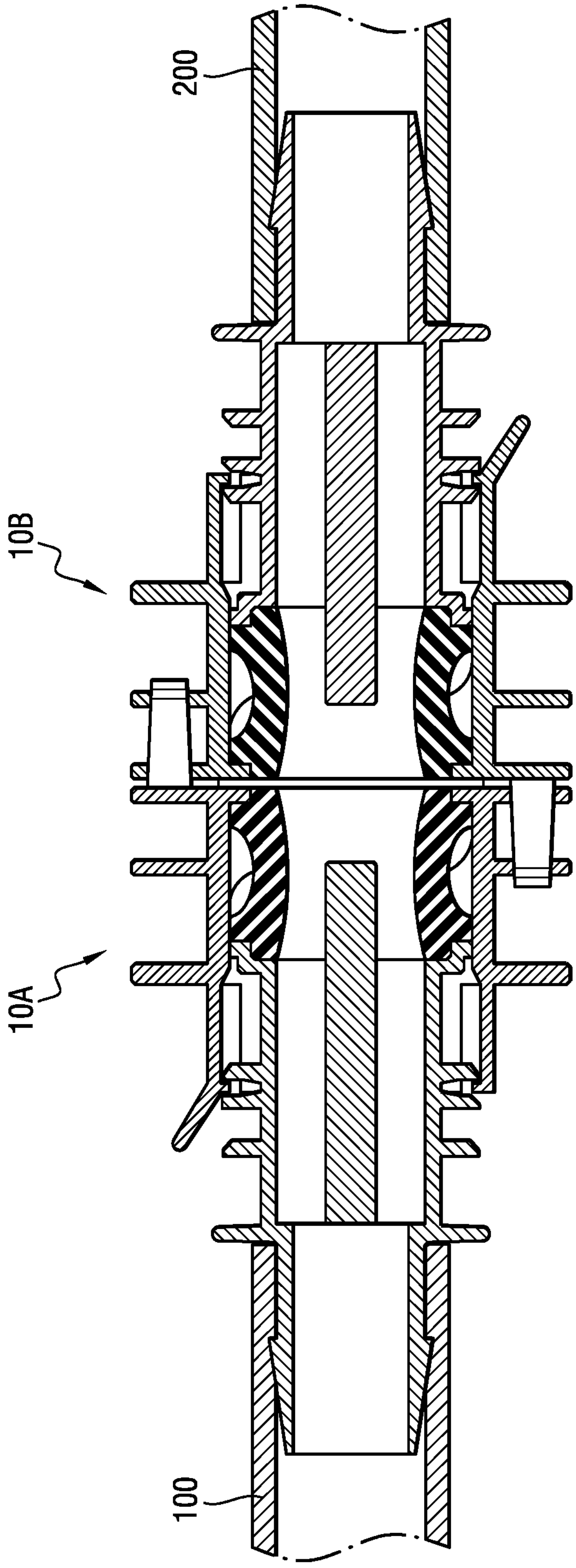
FIG. 4B is a view analogous to FIG. 4A during connection, prior to removing the protective film.

On continuing to move the first and second devices 10A and 10B towards each other, the protective films 50 are pressed against the front faces 35 of the bodies 30 as formed by the lips 33 and by the first fins 34.1, thereby lightly compressing end portions of the sealing elements 40 projecting from said front faces and also causing the first serrations 36.1 of the locking tabs 36 of the first device 10A to co-operate with the edges of the second openings 37.2 of the second device 10B, and causing the first serrations 36.1 of the locking tabs 36 of the second device 10B to co-operate with the edges of the second openings 37.2 of the first device 10A (FIG. 4B). This is said to constitute "pre-coupling" of the first and second devices 10A and 10B.

Figure 4C:
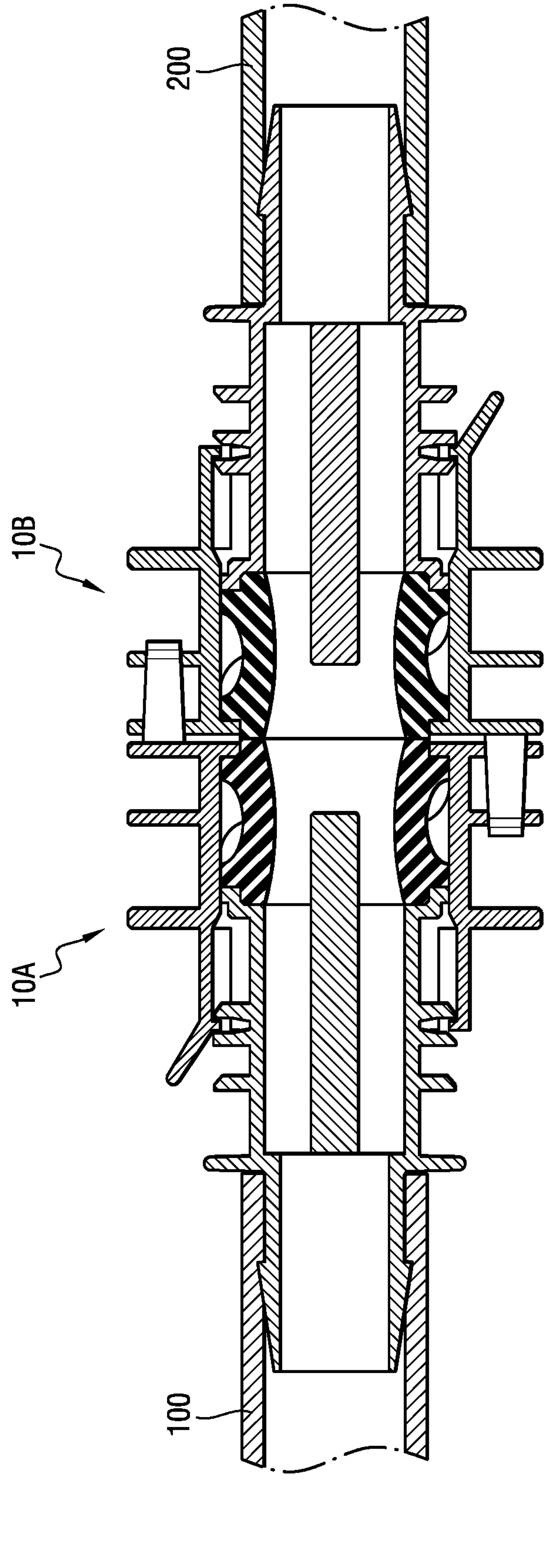
FIG. 4C is a view analogous to FIG. 4A during connection, after to removing the protective film.

The protective films 50 are then removed by passing the same finger through the holes 51.1 in the tongues 51 of the first and second devices 10A and 10B and by pulling simultaneously on said tongues 51, thereby decompressing the end portions of the sealing elements and putting them into leaktight contact with each other (FIG. 4C).

Figure 4D:
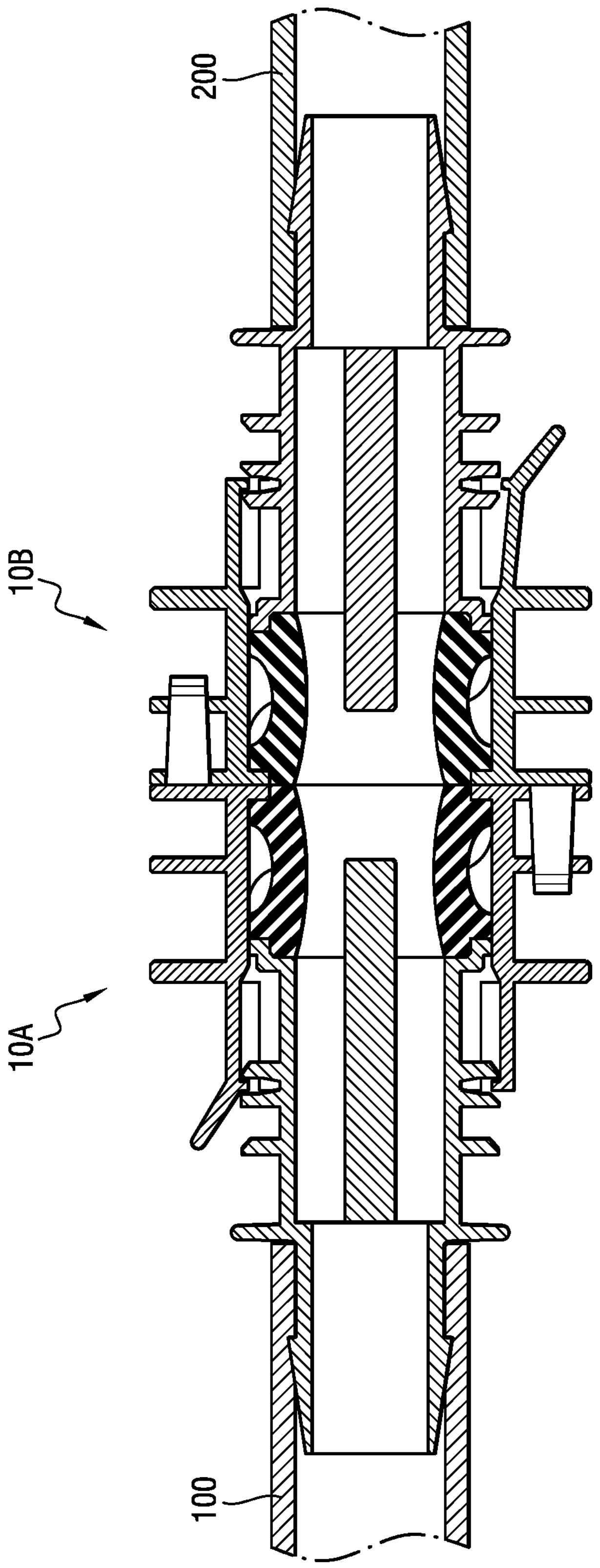
FIG. 4D is a view analogous to FIG. 4A after connection.

The first and second devices 10A and 10B are then moved towards each other for a last time in order to press the front faces 35 of the bodies 30 against each other, thereby once more lightly compressing the end portions of the sealing elements 40 and causing the second serrations 36.2 of the locking tabs 36 to co-operate with the edges of the second openings 37.2 (FIG. 4D). This is said to constitute "coupling" of the first and second devices 10A and 10B, which together then form a channel for passing a fluid between the first tube 100 and the second tube 200.

Figure 5A:
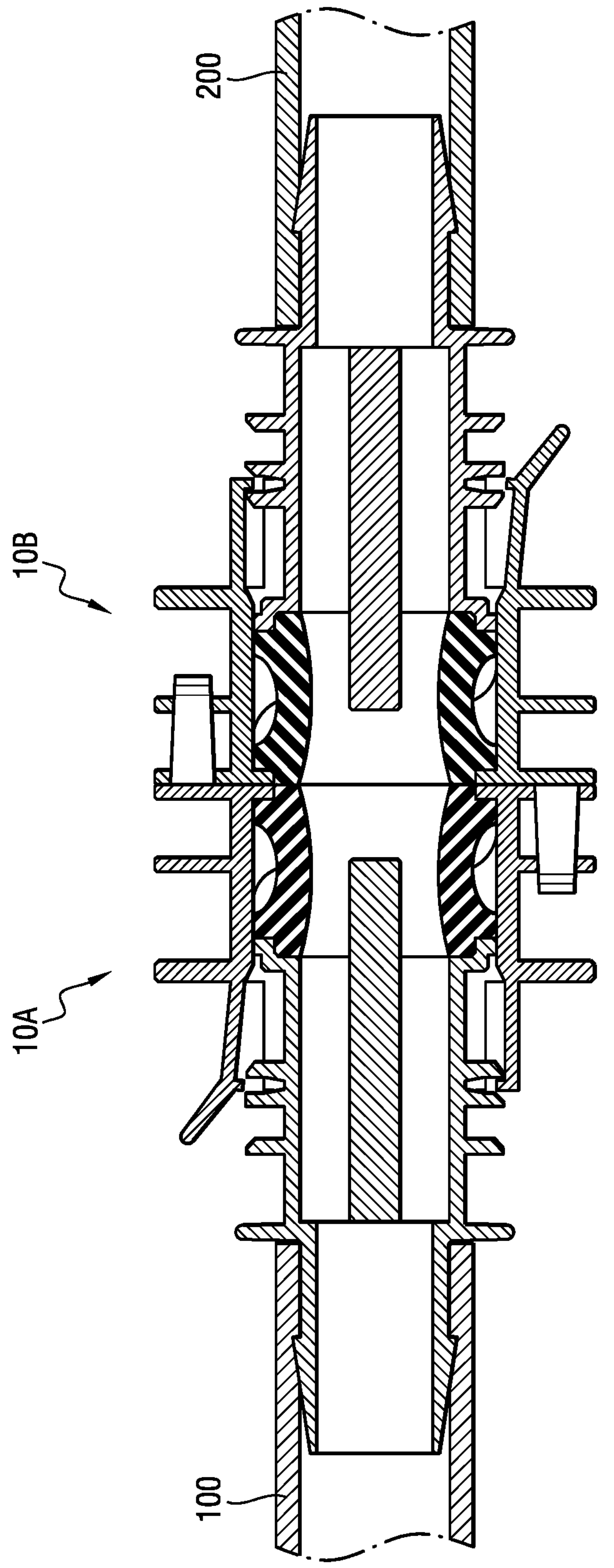
FIG. 5A is a view analogous to FIG. 4D, prior to disconnection.

When it is appropriate to disconnect the first device 10A from the second device 10B, a lifting force is initially applied to the extensions 31.2 of the first blades 31 of the bodies 30 so as to bring said blades 15 into their deformed state and thus allow the bodies 30 to be moved axially towards the flush position (FIG. 5A).

Figure 5B:
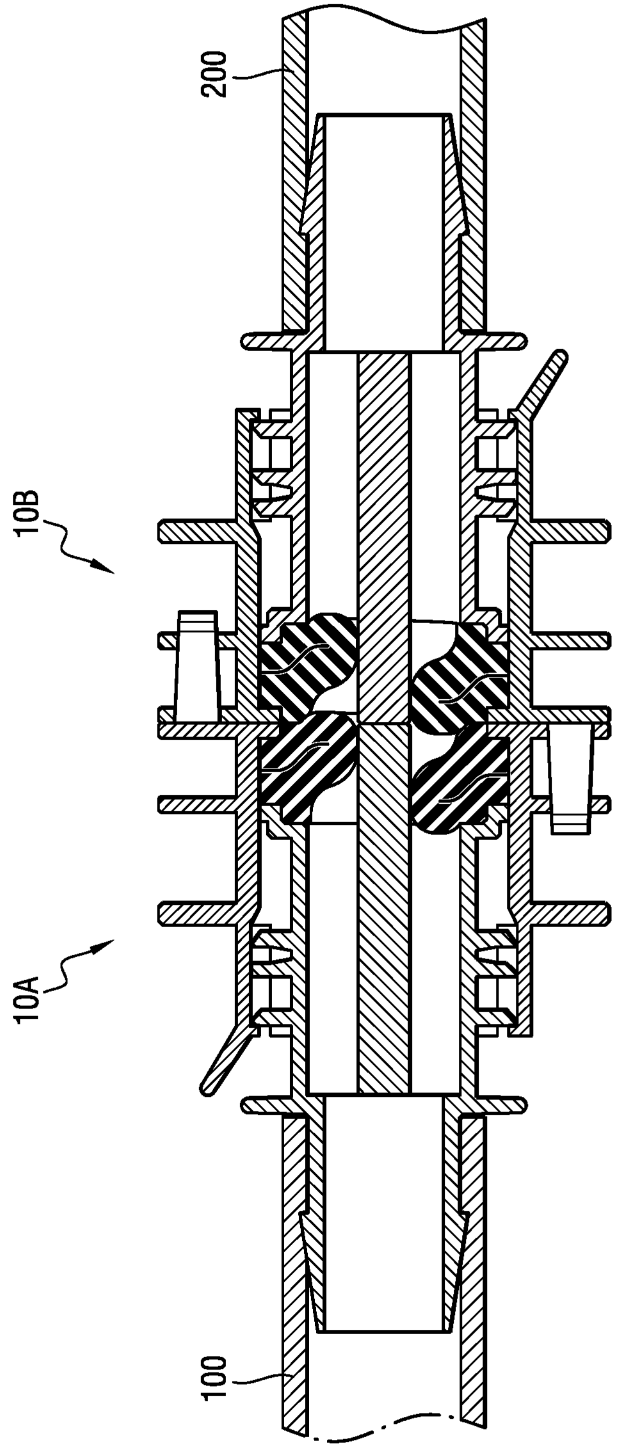
FIG. 5B is a view analogous to FIG. 5B during disconnection.

Axial force is then exerted on the inserts 20, e.g. via the tubes 100 and 200, so as to bring the bodies 30 into the flush position and thereby compress the sealing elements 40 sufficiently for them to surround the rods 25 of the inserts 20 tightly (FIG. 5B). The free ends of the end portions 25.1 of the rods 25 are then substantially in contact, and the fluid can no longer flow between the first tube 100 and the second tube 200, and more particularly between the first device 10A and the second device 10B.

The teeth 31.1 of the first blades have then gone past the second detent rings 28.2, the lifting force exerted on said first blades is stopped, and the teeth 31.1 no longer oppose movement of the bodies 30 towards the flush position.

Figure 5C:
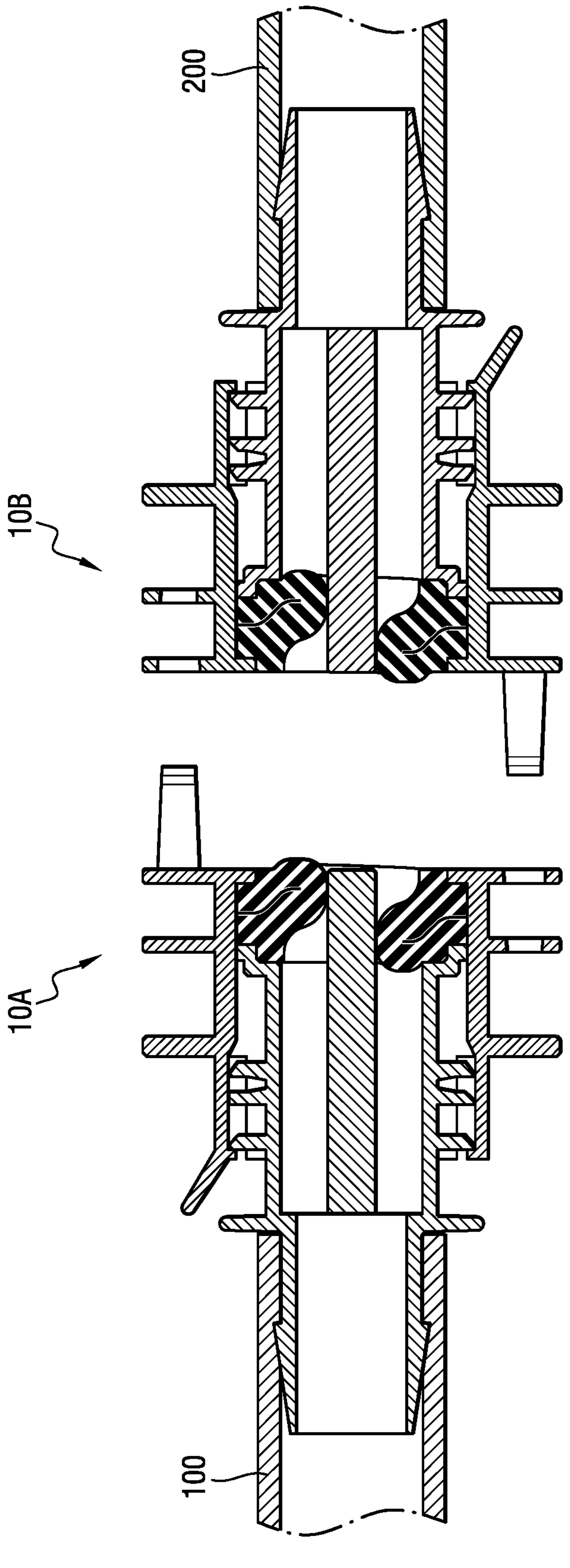
FIG. 5C is a view analogous to FIG. 5A, after disconnection.

Once in the flush position, the teeth 31.1 and 31.2 oppose axial movement of the bodies 30 towards the projecting position as a result of forces generated by the sealing elements 40 being compressed. A pinching force is then exerted simultaneously on the locking tabs 36 of the first device 10A and on the locking tabs 36 of the second device 10B so as to deform said locking tabs 36 elastically and enable the bodies 30 to be separated from each other (FIG. 5C). The sealing elements 40 tightly surrounding the rods 25 thus serve to prevent the fluid that remains trapped in the tubes 100 and 200 from flowing when the devices 10A and 10B are disconnected.

Naturally, the invention is not limited to the implementation described, but covers any variant coming within the ambit of the invention as defined by the claims.

Although above, the coupling assembly comprises two devices 10A and 10B that are identical, it could equally well comprise two devices that are different. For example, the locking tabs 36 of the first device 10A could be replaced by openings, and the openings 37.1 and 37.2 of the second device could be replaced by locking tabs so as to form a male connector and a female connector.

Although above, the devices 10A and 10B are coupled together by clip fastening, they could equally well be coupled together by any other means such as screwing a portion of the device 10A onto the other device 10B.

Although above, the tubes 100 and 200 are anchored to the devices 10A and 10B by a spigot-shaped projection, they could equally well be anchored by any other means such as a snap ring, a washer with external teeth, or elastically deformable arms.

Although above, the body 30 is locked in the projecting position and in the position by using detent rings, it could equally well be locked in position by any other means such as by using pegs.

Although above, the sealing element is symmetrical, it need not be symmetrical.

The steps for disconnecting the devices 10A and 10B may be performed simultaneously on both of the devices 10A and 10B, or else they may be performed on one of the devices and then on the other.

The invention claimed is:

1. An aseptic coupling device for a tube characterized in that it comprises:

- a tubular insert defining a channel and having both a first end segment provided with means for connecting it to the tube and also a second end segment for extending outside the tube, the tubular insert being provided with a cantilevered rod extending axially inside the channel so as to have a free end portion projecting out from the second end segment of the insert, wherein the channel is configured to transmit a flow of fluid so that the fluid contacts an exterior surface of the rod; and
- an annular body comprising both a first end segment mounted on the second end segment of the insert and also a second end segment projecting axially from the second end segment of the insert so as to co-operate therewith to define a housing in register with the free end portion of the rod for receiving an annular sealing element that is placed between a front face of the second end segment of the insert and an internal lip of the second segment of the annular body and that is deformable between a first state in which the sealing element defines a fluid flow section greater than the cross section of the rod and a second state in which the sealing element tightly surrounds the rod, the sealing element being arranged to be taken from its first state to its second state under the effect of axial compression;

and in that:

- the sealing element has a front face projecting from the second segment of the annular body with a protective film removably fastened thereto, the film having a pull-tongue folded down thereon with a first end connected to an edge of the protective film and a second end projecting from the edge of the film that is opposite from the first end of the pull-tongue; and
- the first end segment of the body is mounted on the insert so as to be movable axially between a projecting position in which it projects axially from the insert and in which the sealing element is in its first state, and a flush position in which it is flush with the insert and in which the sealing element is compressed axially sufficiently to be in its second state, wherein the second state seals the sealing element against the rod to prevent the fluid from flowing through the channel along the exterior surface of the rod.

2. A device according to claim 1, including locking means for locking the body in its projecting position and in its flush position.

3. A device according to claim 1, including pre-coupling and coupling means for engaging another coupling device.

4. A device according to claim 3, wherein the pre-coupling and coupling means comprise at least one locking tab projecting axially from a front face of the body and including at least two serrations at a free end for co-operating with an edge of the other coupling device.

5. A coupling assembly for coupling together two tubes, the coupling assembly comprising two coupling devices according to claim 1.

6. An assembly according to claim 5, wherein the two coupling devices are identical.

7. A method of connecting together two tubes by means of a coupling assembly according to claim 5, the method comprising the following steps:

- placing the devices to face each other axially;
- moving the devices towards each other until the pull-tongues are in contact with each other and the protective films are pressed against the front faces of the bodies;
- removing the protective films by pulling simultaneously on the pull-tongues; and
- moving the devices towards each other again until the bodies are pressed against each other.

* * * * *